United States Patent [19]

Aungst et al.

[11] Patent Number: 4,626,539
[45] Date of Patent: Dec. 2, 1986

[54] TRANDERMAL DELIVERY OF OPIOIDS

[75] Inventors: Bruce Aungst; Robert C. DiLuccio, both of Wilmington, Del.

[73] Assignee: E. I. DuPont de Nemours and Company, Wilmington, Del.

[21] Appl. No.: 741,762

[22] Filed: Jun. 10, 1985

Related U.S. Application Data

[63] Continuation-in-part of Ser. No. 639,385, Aug. 10, 1984, abandoned.

[51] Int. Cl.$^4$ ............................................. A61K 31/44
[52] U.S. Cl. ................................................... 514/282
[58] Field of Search ......................................... 514/282

[56] References Cited

U.S. PATENT DOCUMENTS

| | | | |
|---|---|---|---|
| 3,275,510 | 9/1966 | Magid et al. | 514/174 |
| 3,592,930 | 7/1971 | Katz et al. | 514/172 |
| 3,867,528 | 2/1975 | Ritter et al. | 514/174 |
| 3,888,995 | 6/1975 | Katz et al. | 514/172 |
| 3,924,004 | 12/1975 | Chang et al. | 514/172 |
| 4,091,090 | 5/1978 | Sipos | 424/45 |
| 4,299,826 | 11/1981 | Luedders | 514/174 |
| 4,405,616 | 9/1983 | Rajadhyaksha | 424/45 |
| 4,416,886 | 11/1983 | Bernstein | 514/172 |

OTHER PUBLICATIONS

*Contact Dermatitis*, 1, pp. 65–69, M. A. Stillman et al., (1975).

Primary Examiner—Stanley J. Friedman

[57] ABSTRACT

Opioid-containing pharmaceutical compositions are provided which are useful in effecting transdermal delivery of a therapeutic dose of the opioid to the systemic circulation of a mammal. These pharmaceutical compositions consist essentially of the opioid, a penetration enhancer which is at least one of a saturated fatty alcohol or fatty acid of 8–15 carbon atoms or of an unsaturated fatty alcohol or fatty acid of 8–18 carbon atoms, and a suitable pharmaceutical carrier, preferably propylene glycol.

27 Claims, No Drawings

TRANDERMAL DELIVERY OF OPIOIDS

RELATED APPLICATION

This application is a continuation-in-part of application U.S. Ser. No. 639,385 filed Aug. 10, 1984, now abandoned.

BACKGROUND OF THE INVENTION

This invention relates to opioid-containing pharmaceutical compositions which are useful in effecting transdermal delivery of a therapeutic dose of the opioid to the systemic ciruclation of a mammal.

Many opioids are known to have poor bioavailability in the mammalian systemic circulation due to extensive initial metabolism of the drug by the liver and intestines. Furthermore, the bioavailability of orally administered opioids may be unpredictable since various factors such as changes in acidity and food content can cause changes in the amount of drug absorbed from the gastrointestinal tract. Also, oral administration does not necessarily insure good patient compliance.

Parenteral administration of opioids provides better bioavailability than oral administration. However, the various routes of parenteral administration such as intravenous, intramuscular, and subcutaneous delivery are not convenient for chronic therapy. This is particularly true for those opioids which exhibit short biological activity half-lives.

Topical formulations of opioids do not necessarily provide delivery of a therapeutic dose of the drug to the systemic circulation and thus provide poor or unpredictable bioavailability.

Transdermal delivery of opioid drugs to the mammalian systemic circulation would be an alternative mode of administration which could provide the following advantages:

1. Improved and predictable bioavailability of the opioid as compared to oral administration since transdermal delivery avoids initial metabolism by the liver and intestines, and unpredictable absorption from the gastrointestinal tract.

2. A stable blood serum level of the drug resulting in a prolonged pharmacological effect similar to intravenous infusion.

3. Easily adjustable dosing rate which provides maximization of efficacy and minimization of side effects.

4. Easily removable drug source which provides rapid cessation of dosing and elimination of the drug from the body fluids.

5. Convenience of dosing which provides improved patient comfort as compared to parenteral administration and the possibility of greater patient compliance as compared to oral administration.

Transdermal drug delivery is distinguished from topical drug delivery by the fact that while a transdermal formulation is specifically designed to provide a predictable and therapeutically significant rate of delivery of the drug to the systemic circulation, a topical formulation is specifically designed to provide a therapeutic effect only to the local area to which the drug is applied. Furthermore, topical formulations are often designed to prevent any systemic delivery of the drug in order to minimize side-effects. However, even if the topical delivery of a drug does result in systemic absorption, the amount of drug delivery to the circulation is variable and uncontrolled.

The skin is an excellent barrier to the penetration of many foreign substances. The feasibility of using transdermal delivery of opioid drugs as a route of administration requires that a therapeutic rate of drug delivery through the skin be achieved. This can be accomplished if the skin can be made more permeable to the drug.

Factors which determine the permeability of the skin to a particular drug include drug diffusivity through the skin membrane, vehicle/skin drug partitioning, and drug concentration in the vehicle. In addition, certain materials used as adjuvants in vehicles may affect the characteristics of the skin membrane barrier and thus alter the permeability of the skin to the drug. Such materials are referred to as skin penetration enhancers. These penetration enhancers are important in the optimization of transdermal drug delivery because of the necessity for maximization of penetration rates and minimization of lag times in the drug penetration through the skin.

The permeability of the skin to a drug is influenced by a combination of physico-chemical parameters for both the drug and the vehicle, as discussed above. Thus, effective transdermal delivery of a particular class of drugs requires the selection of an appropriate vehicle. The optimum vehicle for one class of drugs may not be effective for transdermal delivery of another class of drugs since the properties of the vehicle and the drug must be matched to insure a therapeutic rate of drug delivery through the skin.

Ritter et al., U.S. Pat. No. 3,867,528, issued Feb. 18, 1975, disclose pharmaceutical compositions comprising ethoxylated stearyl alcohol and steroids which provide greater penetration of the steriod through the skin to produce greater topical therapeutic activity. The disclosed composition is shown to provide greater penetration of the steroid than other topical formulations, but there is no indication as to which ingredient in the disclosed formulation contributed to the enhanced penetration. There is no disclosure that stearyl alcohol is effective in producing transdermal delivery of a therapeutic dose of an opioid to the systemic circulation.

Katz et al., U.S. Pat. No. 3,592,930, issued July 13, 1971; Katz et al., U.S. Pat. No. 3,888,995, issued June 10, 1975; and Chang et al., U.S. Pat. No. 3,924,004, issued Dec. 2, 1975, disclose pharmaceutical compositions comprising corticoids and from 5 to 40 percent saturated fatty alcohol having from 16 to 24 carbons. The alcohol is used as a vehicle for the topical administration of the anti-inflammatory corticoid. There is no disclosure that the fatty alcohol is effective in producing transdermal delivery of a therapeutic dose of the steroid to the systemic circulation, or that the alcohol would make the skin more permeable to opioids.

Magid et al., U.S. Pat. No. 3,275,510, issued Sept. 27, 1966, disclose topical antitussive formulations comprising a mixture of an orally active antitussive agent and a lipophilic or hydrophilic carrier. The disclosed antitussive agents include codeine, dihydrocodeinone, 1-α,2-methyl-8-methoxy-6,7-methylenedioxy-1-(6,7-dimethoxy-3-phthalidyl)-1,2,3,4-tetrahydroisoquinolone, α-(dimethylaminoethyl)-o-chlorobenzhydrol, d-3-methoxy-N-methylmorphinan and medically acceptable acid addition salts thereof. There is no disclosure or suggestion that the disclosed formulations contain any particular penetration enhancer(s), that the rate of systemic delivery of the antitussive agents can be controlled, that the disclosed formulations would be useful for compounds which are not orally active, or that the disclosed formulations would be effective for any indication other than as antitussives.

Sipos, U.S. Pat. No. 4,091,090, issued May 23, 1978, discloses topical anesthetic compositions wherein there is obtained an enhancement of the activity of the topical anesthetic agent by combining the anesthetic agent with an effective amount of a penetrant accelerator cyclohexyl alkanol. The compositions are shown to exhibit quicker onset and deeper anesthesia at the site of application. The effect, however, is still a local anesthesia and there is no disclosure that these alcohols effect systemic delivery of the anesthetic or that these alcohols or fatty alcohols and fatty acids would be effective in producing transdermal delivery of a therapeutic dose of an opioid.

Luedders, U.S. Pat. No. 4,299,826, issued Nov. 10, 1981, discloses topically applied, anti-acne pharmaceutical compositions which comprise an erythromycin compound and a pharmaceutically acceptable penetrating carrier wherein said carrier comprises a penetration enhancing amount of diisopropyl sebacate and a dermatologically acceptable alcohol. There is no disclosure or suggestion that the carrier components would make the skin more permeable to opioids.

Rajadhyaksha, U.S. Pat. No. 4,405,616, issued Sept. 20, 1983, discloses a method for administering systemically active agents including analgesics, analgesic combinations, and anorexics, through the skin in a transdermal device or formulation. The skin penetration enhancers, disclosed as achieving transdermal delivery of the systemically active agents, are lactams such as 1-dodecylazacycloheptan-2-one. The utility of fatty acids or fatty alcohols as penetration enhancers for opioids is not disclosed or suggested.

Bernstein, U.S. Pat. No. 4,416,886 (Bernstein), issued Nov. 22, 1983, discloses a method for treating severe pruritis which comprises the topical administration of a solution, lotion, cream or ointment comprising naloxone or naltrexone. The patent discloses that the liquid dosage forms for the topical administration of naloxone or naltrexone comprise volatile diluents such as alcohol and glycol. There is no disclosure or suggestion that the alcohol or glycol is effective in producing transdermal delivery of a therapeutic dose of naloxone or naltrexone to the systemic circulation. There is also no disclosure or suggestion that even an appreciable amount of naloxone or naltrexone is delivered to the systemic circulation since the antipruritic effect is a local effect.

Michael A. Stillman et al., Relative irritancy of free fatty acids of different chain length, *Contact Dermatitis*, 1, 65–69 (1975), found that the most irritating fatty acids to human skin were $C_8$ to $C_{12}$.

There is a need for opioid-containing vehicles which are effective in the transdermal delivery of a therapeutic dose of the drug to the mammalian systemic circulation. The opioid-containing pharmaceutical compositions of the instant invention fulfill this need.

SUMMARY OF THE INVENTION

The present invention relates to a pharmaceutical composition effective in producing transdermal delivery of a therapeutically effective amount of an opioid to the mammalian systemic circulation, the composition consisting essentially of a therapeutically effective amount of an opioid or a pharmaceutically acceptable salt thereof; an effective penetration enhancing amount of at least one of a saturated fatty alcohol or fatty acid of 8–15 carbon atoms or of an unsaturated fatty alcohol or fatty acid of 8–18 carbon atoms; and a suitable pharmaceutical carrier.

The present invention also relates to a method of administering a therapeutic dose of an opioid to the systemic circulation of a mammal which comprises the topical administration of an opioid-containing pharmaceutical composition, wherein the composition consists essentially of a therapeutically effective amount of an opioid or a pharmaceutically acceptable salt thereof; an effective penetration enhancing amount of at least one of a saturated fatty alcohol or fatty acid of 8–15 carbon atoms or of an unsaturated fatty alcohol or fatty acid of 8–18 carbon atoms; and a suitable pharmaceutical carrier.

DETAILED DESCRIPTION OF THE INVENTION

By the term "opioid" is meant any natural or synthetic opioid analgesic such as morphine, oxymorphone, fentanyl, meperidine, propoxyphene, or oxycodone; any natural or synthetic narcotic antagonist such as nalmefene, naloxone or naltrexone; any natural or synthetic mixed opioid agonist/antagonist such as nalbuphine, butorphanol, buprenorphine or pentazocine; or any pharmaceutically acceptable salt thereof.

By the term "pharmaceutically acceptable salt" is meant any non-toxic pharmaceutically suitable salt of an opioid which has therapeutic properties in mammals. Preparation of such salts is well known to those skilled in pharmaceuticals. Pharmaceutically acceptable salts of opioids include acetates, napsylates, tosylates, succinates, hydrochlorides, palmitates, stearates, oleates, pamoates, laurates, valerates, hydrobromides, sulfates, methane sulfonates, tartrates, citrates, and maleates.

By the term "fatty alcohol or fatty acid" is meant any saturated fatty acid or fatty alcohol having from 8 to 15 carbon atoms or any unsaturated fatty acid or fatty alcohol having from 8 to 18 carbon atoms which is effective in enhancing the penetration of an opioid through the mammalian skin. In addition, any combination of fatty acids and fatty alcohols having the above specified number of carbon atoms which is effective in enhancing transdermal opioid penetration may be used. Preferred penetration enhancing fatty acids and fatty alcohols are those with 10–15 carbon atoms or any mixture thereof. Especially preferred penetration enhancing fatty acids and fatty alcohols are those with 14 carbons such as myristic acid and myristyl alcohol. It should be understood that the terms "penetration enhancer" and "fatty acid or fatty alcohol" will be used interchangeably throughout the remainder of the instant specification.

By the term "suitable pharmaceutical carrier" is meant any non-toxic pharmaceutically suitable vehicle which comprises any polar protic solvent with a molecular weight of less than 600. Suitable carriers include propylene glycol or polyethylene glycol. Propylene glycol is a preferred carrier or vehicle, and any other carriers which may be used are then considered as excipients.

All starting materials useful in making the pharmaceutical compositions of the instant invention are known.

The pharmaceutical composition of the present invention may be in lotion or cream form, and can have the composition shown in Table A. All concentrations are given herein as weight percent unless otherwise specified.

TABLE A

| Ingredient | Concentration | Preferred Concentration |
| --- | --- | --- |
| (1) Opioid | 1 to 15% | 5 to 15% |
| (2) Vehicle | 30 to 80% | 30 to 80% (propylene glycol) |
| (3) Penetration Enhancer* | 1 to 45% | 2 to 25%** |
| (4) Excipients | To 100% total | To 100% total |

*$C_8$ to $C_{15}$ saturated fatty acid or fatty alcohol or $C_8$ to $C_{18}$ unsaturated fatty acid or fatty alcohol or any mixture thereof
**$C_{10}$ to $C_{15}$ fatty acid or fatty alcohol or any mixture thereof.

The physical properties of the pharmaceutical compositions of this invention can be modified by selecting fatty acids or alcohols with various melting points to provide either lotions or creams. The vehicle chosen will also effect the consistency of the pharmaceutical composition. To increase the viscosity of the lotion, or to thicken the composition to provide a cream, the percent composition of higher melting fatty acids and fatty alcohols, such as stearyl alcohol, cetyl alcohol or stearic acid, should be increased.

In addition, the pharmaceutical compositions of this invention, such as those shown in Table A, may further comprise water and an emulsifying agent (such as acacia, lecithin, and other pharmaceutically acceptable nonionic or ionic surfactants, 0.1 to 10% w/w) to provide compositions in emulsion form which contain from about 30 to 50% water.

Alternatively, a composition such as that shown in Table A may be mixed with a polymeric substance such as ethylcellulose, hydroxypropylcellulose or a mixture thereof to provide compositions in a gel form which contain from about 20 to 30% polymeric substance. These gels may then be dissolved in a suitable solvent such as methylene chloride, evaporated to the desired viscosity, and applied to a backing material to provide a patch.

Utility

The pharmaceutical compositions of the instant invention can be administered transdermally to provide continuous delivery of the opioid component to the systemic circulation of a mammal and thus maintain constant therapeutic levels of the opioid. Thus, the pharmaceutical compositions of the instant invention provide an alternative to oral or parenteral administration of opioids.

In oral and parenteral routes of delivery, in order to compensate for the normal biological elimination processes, it is often necessary to administer larger doses of the drugs to achieve therapeutic serum levels. In the case of opioid drugs, particularly potent opioid analgesics, the more the dose is increased, the more the danger of serious side effects, such as respiratory depression, are increased. Transdermal delivery of the opioid-containing pharmaceutical compositions of the instant invention provides an advantage over oral and parenteral administration of the drug by maintaining a relatively constant blood level of the active ingredient which allows for better control of side effects. Thus, while the pharmaceutical compositions of the instant invention are useful in the treatment of any condition in which the opioid ingredient is indicated, they are particularly useful in those cases where prolonged treatment is indicated. Thus, if the opioid component is an analgesic, the compositions would be useful for the treatment of severe and chronic pain in cancer patients. If the opioid component is a narcotic antagonist, the compositions would be useful for the treatment of obesity or shock, sexual dysfunction, cognitive disorders, stroke, or after the initial injection, in the treatment of narcotic overdose.

The compositions of the instant invention were evaluated for their ability to deliver opioids to the systemic circulation of mammals by measuring the flux of drug and lag time across hairless mouse and human cadaver skin in vitro using diffusion cells. The concentration of the opioid diffusing through the skin was determined by radioisotope counting or by high pressure liquid chromatography analysis. The lag time determined represents the time required before drug first appeared on the other side of the skin.

Vehicle

Drug penetration through skin was first evaluated using naloxone in a variety of vehicles (Table 1). Vehicles which provided the highest naloxone fluxes through skin included propylene glycol, isopropanol, ethanol, oleic acid and N-methylpyrrolidone. Nonaqueous vehicles provided higher fluxes of naloxone than aqueous vehicles.

Penetration Enhancers

Potential skin penetration enhancers were evaluated primarily using propylene glycol as the vehicle with the addition of 10% adjuvant (Table 2). While several fatty acids and fatty alcohols were found to enhance naloxone skin penetration, the fatty acid esters did not affect naloxone flux.

The results given in Table 2 demonstrate that very substantial increases in the transdermal penetration of naloxone can be obtained by the addition of a penetration enhancer to a pharmaceutical composition comprising naloxone. The formulations of the Bernstein reference do not disclose any penetration enhancers, and would presumably deliver approximately as much naloxone as the propylene glycol control formulations in Table 2.

A variety of fatty acids and fatty alcohols were evaluated for their penetration enhancing ability through hairless mouse skin (Table 3). Maximum penetration enhancement was observed for fatty acids and fatty alcohols with 12 carbons. However, significant skin irritation resulted from fatty acids and fatty alcohols of 12 carbons or less. Fatty acids and fatty alcohols of 14 carbons show the best balance of high flux and minimum skin irritation and therefore were selected as optimum skin penetration enhancers. Also, the penetration enhancing effect increased as the unsaturation of the fatty acid and fatty alcohol molecule increased.

Gels

Various gels containing ethylcellulose, ethylene/vinylacetate, and polyvinylpyrrolidone (PVP) were evaluated (Tables 4, 5 and 6).

Formulations containing oleic acid and propylene glycol were gelled with various polymers including ethylcellulose, ethylene/vinylacetate, and PVP. Tables 4 and 5 demonstrate that high naloxone fluxes can be obtained with gel formulations containing ethylene/vinylacetate. Often, addition of a polymer will result in a decrease in the penetration of the drug as was found with PVP (Table 6).

The availability of gels which provide transdermal delivery of a therapeutically effective amount of an opioid to the systemic circulation permits the preparation of "patches" which provide a convenient method of effecting sustained delivery of the opioids.

Emulsions

Emulsions containing naloxone HCl in water as the aqueous phase, propylene glycol, an emulsifying agent, and a fatty acid were prepared and evaluated (Table 7). Very high naloxone fluxes would be obtained with these formulations as well.

Other Opioids

Gels containing propylene glycol; fatty acids and/or fatty alcohols; ethylcellulose or hydroxypropylcellulose or a mixture thereof; and the opioid oxymorphone, nalbuphine, or naltrexone; were prepared and evaluated (Tables 8 and 9). These results indicate that a therapeutically effective dose of an opioid can be delivered to the systemic circulation of a mammal using the pharmaceutical compositions of the instant invention. Comparison of the results of Table 8 with those of propylene glycol control demonstrates that the compositions of the instant invention provide greatly enhanced transdermal penetration as compared to compositions containing no penetration enhancer.

The term "consisting essentially of" as used in the present disclosure is intended to have its customary meaning, namely, that all specified material and conditions are very important in practicing the invention but that unspecified materials and conditions are not excluded so long as they do not prevent the benefits of the invention from being realized.

TABLE 1

EFFECT OF VEHICLE ON [$^3$H] NALOXONE PENETRATION THROUGH HUMAN SKIN IN VITRO (MEAN + S.E.)

| Vehicle | Naloxone Concentration (mg/ml) | N[b] | Flux ($\mu$g/cm$^2$ hr.) | Lag Time (Hours) |
|---|---|---|---|---|
| Dimethylpolysiloxane | 0.4* | 2 | 0.3 | |
| Mineral oil | 0.4* | 2 | 0.2 | |
| Sesame oil | 6.3* | 2 | 2.7 | |
| Olive oil | 7.1* | 2 | 3.5 | |
| Polyethylene Glycol 400 | 30 [87][a] | 4 | 3.4 ± 0.6 | 8.4 ± 1.9 |
| Isopropanol | 30 [46][a] | 4 | 9.8 ± 0.5 | 1.1 ± 0.9 |
| Propylene Glycol | 30* | 13 | 12.1 ± 2.7 | 16.8 ± 1.8 |
| Ethanol | 30 [72][a] | 2 | 25.2 | 5.0 |
| Oleic Acid | 30 | 4 | 16.4 ± 1.4 | 0.5 ± 0.3 |
| Oleic Acid | 120* | 2 | 70.0 | |
| N—Methylpyrrolidone | 30 | 2 | 32.9 | |
| N—Methylpyrrolidone | 300 [400][a] | 2 | 220 | |
| TRIS Buf-pH8 | 0.3 [0.9][a] | 14 | 0.4 ± 0.1 | 6.5 ± 2.1 |

*Solubility Limit
[a]Solubility limits for other solvents are within brackets
[b]N = Number of tests

TABLE 2

EFFECTS OF ADJUVANTS ON [$^3$H] NALOXONE PENETRATION THROUGH HUMAN SKIN IN-VITRO

| Adjuvant (10% in PG[a]) | Naloxone Conc. (mg/ml) | N[b] | Flux ($\mu$g/cm$^2$ Hr) | Lag Time (Hr.) |
|---|---|---|---|---|
| PG Control[c] | 0.3 | 13 | 0.3 ± 0.1 | 16.5 ± 2.6 |
| Isopropyl Palmitate | 0.3 | 2 | 0.1 | 6.8 |
| Isopropyl Myristate | 0.3 | 2 | 0.2 | 6.6 |
| Ethyl Myristate | 0.3 | 1 | 0.2 | — |
| 1-Dodecanol | 0.3 | 2 | 1.9 | 4.0 |
| 2-Dodecanol | 0.3 | 2 | 0.7 | 4.6 |
| PG Control | 30 | 13 | 12.1 ± 2.7 | 16.8 ± 1.8 |
| Oleic Acid | 30 | 2 | 34.9 | 5.3 |
| Oleyl Alcohol | 30 | 2 | 46.4 | 2.1 |
| 2-Dodecanol | 30 | 2 | 87.0 | 1.8 |

[a]PG = propylene glycol
[b]N = number of tests
[c]PG Control - saturated propylene glycol solution containing no penetration enhancer

TABLE 3

[$^3$H] NALOXONE PENETRATION THROUGH HAIRLESS MOUSE SKIN USING PROPYLENE GLYCOL WITH 10% (v/v) ADJUVANT AND 30 mg/ml NALOXONE

| Adjuvant | Length of Chain: # of Double Bonds | N[a] | Flux ($\mu$g/cm$^2$ Hr.) | Lag Time (Hours) |
|---|---|---|---|---|
| Control | — | 2 | 20.5 | 17.7 |
| Caprylic Acid | 8:0 | 2 | 360.1 | 3.3 |
| Octanol | 8:0 | 2 | 208.1 | 4.0 |
| Capric Acid | 10:0 | 2 | 305.5 | 1.2 |
| Decanol | 10:0 | 2 | 361.4 | 1.4 |
| Lauric Acid | 12:0 | 2 | 328.2 | 1.1 |
| 1-Dodecanol | 12:0 | 2 | 377.0 | 0.4 |
| 2-Dodecanol | 12:0 | 2 | 339.0 | 0.8 |
| Myristic Acid | 14:0 | 2 | 71.8 | 3.1 |
| Myristyl Alcohol | 14:0 | 2 | 189.1 | 1.6 |
| Palmitic Acid | 16:0 | 2 | 45.5 | 6.4 |
| Palmityl Alcohol | 16:0 | 2 | 25.4 | 12.3 |
| Stearic Acid | 18:0 | 2 | 35.8 | 10.0 |
| Stearyl Alcohol | 18:0 | 2 | 33.8 | 10.4 |
| Oleic Acid | 18:1 | 2 | 159.1 | 0.4 |
| Oleyl Alcohol | 18:1 | 2 | 240.6 | 0.2 |
| Linolenic Acid | 18:3 | 2 | 322.5 | 0.3 |
| Linolenyl Alcohol | 18:3 | 2 | 311.9 | 0.6 |

[a]N = number of tests

TABLE 4

NALOXONE PENETRATION THROUGH HUMAN SKIN FROM VARIOUS GEL FORMULATIONS CONTAINING ETHYLCELLULOSE

| Gel | Naloxone | Ethyl-Cellulose | Propylene Glycol | Oleic Acid | Lauric Acid | Dodecanol | Myristic Acid | Flux ($\mu$g/cm$^2$ hr.) | Lag Time (hours) | N[a] |
|---|---|---|---|---|---|---|---|---|---|---|
| (A) | 10 | — | — | 90 | — | — | — | 16.6 ± 7.4 | 11.2 ± 2.4 | 6 |
| (B) | 6–13 | 19–31 | — | 59–72 | — | — | — | 9.4 ± 1.7 | 19.2 ± 3.2 | 14 |
| (C) | 7 | 21 | 64 | 7 | — | — | — | 14.1 ± 2.9 | 2.6 ± 1.8 | 5 |
| (D) | 7–10 | 20–30 | 30–35 | — | 30–35 | — | — | 122.7 ± 24.2 | 22.8 ± 5.7 | 6 |
| (E) | 9–10 | 20–30 | — | 30–35 | 30–35 | — | — | 46.8 ± 3.7 | 31.1 ± 0.3 | 4 |

TABLE 4-continued

NALOXONE PENETRATION THROUGH HUMAN SKIN
FROM VARIOUS GEL FORMULATIONS CONTAINING ETHYLCELLULOSE

| | % Composition | | | | | | Flux | Lag Time | |
|---|---|---|---|---|---|---|---|---|---|
| Gel | Naloxone | Ethyl-Cellulose | Propylene Glycol | Oleic Acid | Lauric Acid | Dodec-anol | Myristic Acid | ($\mu g/cm^2$ hr.) | (hours) | $N^a$ |
| (F) | 7 | 21 | 64 | — | — | 7 | — | 30.1 ± 10.8 | 2.3 ± 1.3 | 5 |
| (G) | 7 | 21 | — | 64 | — | 7 | — | 10.5 | 21.0 | 2 |
| (H) | 7 | 21 | 43 | — | — | 29 | — | 23.6 ± 1.5 | 3.8 ± 1.2 | 3 |
| (I) | 7 | 21 | 43 | — | 14 | 14 | — | 57.9 ± 2.2 | 2.4 ± 1.0 | 3 |
| (J) | 14 | 21 | 36 | — | 14 | 14 | — | 40.8 | 3.2 | 2 |
| (K) | 7 | 36 | 29 | — | 14 | 14 | — | 26.4 | 4.7 | 2 |
| (L) | 7 | 21 | 29 | 14 | 14 | 14 | — | 52.4 | 9.2 | 2 |
| (M) | 7 | 24 | 31 | — | 31 | 7 | — | 53.3 ± 12.4 | 2.4 ± 1.1 | 4 |
| (N) | 10 | 30 | 40 | — | 15 | 5 | — | 58.5 | 0.7 | 2 |
| (O) | 10 | 30 | 40 | — | — | 5 | 15 | 54.9 | 0.4 | 2 |
| (P) | 10 | 35 | 45 | — | 5 | 5 | — | 13.0 | 7.7 | 2 |

$^a$N = number of tests

TABLE 5

NALOXONE PENETRATION THROUGH HUMAN SKIN
FROM GEL FORMULATIONS SUBSTITUTING
ETHYLENE/VINYLACETATE FOR ETHYLCELLULOSE

| Gel$^a$ | Flux ($\mu g/cm^2$ hr.) |
|---|---|
| (M) | 92.2 |
| (N) | 26.6 |
| (O) | 11.8 |
| (P) | 14.4 |

$^a$Formulation is as described in Table 4 but ethylene/vinylacetate polymer has been substituted for ethylcellulose.

TABLE 6

EFFECT OF ADDING POLYVINYLPYRROLIDONE (PVP)
TO ETHYLCELLULOSE GELS$^a$

| % PVP 40,000 | Flux ($\mu g/cm^2$ hr.) |
|---|---|
| 0 | 3.73 |
| 4-6 | 2.91 |
| 8-9 | 1.75 |

$^a$The gels all contained 20% ethylcellulose, 70% oleic acid and 8% naloxone.

TABLE 7

COMPOSITIONS OF NALOXONE HCl EMULSIONS
AND HUMAN SKIN PENETRATION DATA

| | Emulsion | | | | | | | | | |
|---|---|---|---|---|---|---|---|---|---|---|
| % Composition | A | B | C | D | E | F | G | H | I | J |

TABLE 7-continued

COMPOSITIONS OF NALOXONE HCl EMULSIONS
AND HUMAN SKIN PENETRATION DATA

| | A | B | C | D | E | F | G | H | I | J |
|---|---|---|---|---|---|---|---|---|---|---|
| Naloxone HCl | * | * | * | 9 | 9 | 9 | 9 | 9 | 9 | 8 |
| H$_2$O | 48 | 45 | 43 | 45 | 44 | 45 | 44 | 38 | 43 | 40 |
| Propylene Glycol | 24 | 23 | 22 | 20 | 20 | 20 | 20 | 20 | 19 | 18 |
| Lauric Acid | 24 | 23 | 22 | 19 | 16 | 19 | 16 | 22 | 15 | 18 |
| Stearic Acid | — | — | 9 | 4 | 4 | — | 9 | 9 | 4 | 6 |
| Stearyl Alcohol | — | — | — | — | — | 4 | — | — | — | — |
| Dodecanol | — | 5 | — | — | — | — | — | — | 9 | 8 |
| Sucrose Dilaurate | 5 | 5 | 4 | — | — | — | — | — | — | — |
| Propylene Glycol Monolaurate | — | — | — | 2 | 7 | 2 | 2 | 2 | 2 | 2 |

| Emulsion | Naloxone Flux ($\mu g/cm^2$ hr.) | Lag Time (HR.) |
|---|---|---|
| A | 666.3 | 16.8 |
| B | 323.9 | 7.1 |
| C | 177.8 | 9.9 |
| D | 105.1 | 18.7 |
| E | 60.6 | 21.8 |
| F | 291.7 | 23.0 |
| G | 23.1 | 22.1 |
| H | 59.6 | 22.8 |
| I | EMULSION BROKE | |
| J | 17.0 | 22.6 |

*Naloxone HCl added to water above solubility limit.
A 20% solution of naloxone HCl in water gave a flux of 2.1 $\mu g/cm^2$ hr.

TABLE 8

NALBUPHINE, NALTREXONE, AND OXYMORPHONE GEL
COMPOSITION AND HUMAN SKIN PENETRATION DATA

| GEL | DRUG | PROPYLENE GLYCOL | LAURIC ACID | OLEIC ACID | DODECANOL | ETHYL CELLULOSE |
|---|---|---|---|---|---|---|
| A | 7 | 43 | 14 | — | 14 | 21 |
| B | 7 | 57 | — | — | 14 | 21 |
| C | 8 | 33 | 33 | — | — | 25 |
| D | 8 | 31 | 31 | — | 8 | 23 |
| E | 8 | 23 | 15 | 15 | 15 | 23 |

| DRUG | GEL | AVG. FLUX ($\mu g/cm^2$ hr.) | LAG TIME (HR.) |
|---|---|---|---|
| NALBUPHINE | PG control$^a$ | 0.57 | 39.4 |
| | A | 29.9 | 9.4 |
| | B | 3.9 | 17.5 |
| | C | 26.3 | 16.5 |
| | D | 18.6 | 21.0 |
| | E | 8.7 | 26.6 |
| NALTREXONE | PG control$^a$ | — | — |
| | A | 19.2 | 11.6 |
| | B | 29.8 | 3.7 |
| | C | 26.0 | 4.2 |
| | D | 42.1 | 1.6 |
| | E | 13.8 | 4.4 |

TABLE 8-continued

NALBUPHINE, NALTREXONE, AND OXYMORPHONE GEL COMPOSITION AND HUMAN SKIN PENETRATION DATA

| OXYMORPHONE | PG control[a] | 1.88 | 27.6 |
|---|---|---|---|
| | A | 28.4 | 5.7 |
| | B | 12.2 | 14.8 |
| | C | 49.0 | 6.1 |
| | D | 91.5 | 3.3 |
| | E | 62.9 | 27.6 |

[a]PG Control - saturated propylene glycol solution containing no penetration enhancer

TABLE 9

OXYMORPHONE PENETRATION THROUGH HUMAN SKIN FROM VARIOUS GEL FORMULATIONS

| Gel | Oxymorphone | Propylene glycol | Myristic Acid | Dodecanol | Undecylenic Acid | Ethylcellulose | Hydroxypropylcellulose | Flux ($\mu$g/cm$^2$ hr.) | N[a] |
|---|---|---|---|---|---|---|---|---|---|
| (A) | 8 | 63 | — | 5 | — | 24 | — | 22.6 ± 5.8 | 8 |
| (B) | 10 | 55 | 10 | — | — | 25 | — | 29.8 ± 5.6 | 14 |
| (C) | 10 | 55 | — | — | 10 | 25 | — | 14.8 ± 7.0 | 4 |
| (D) | 10 | 60 | 10 | — | — | 20 | — | 32.1 | 2 |
| (E) | 10 | 65 | 10 | — | — | 15 | — | 45.0 | 2 |
| (F) | 10 | 62.5 | 2.5 | — | — | 25 | — | 11.1 | 2 |
| (G) | 10 | 60 | 5 | — | — | 25 | — | 14.8 | 2 |
| (H) | 10 | 50 | 15 | — | — | 25 | — | 26.5 | 2 |
| (I) | 9 | 55 | 9 | — | — | — | 27 | 87.8 ± 11.4 | 10 |
| (J) | 9 | 54 | 9 | — | — | 14 | 14 | 74.0 ± 12.5 | 9 |
| Control | 2.7 | 97.3 | — | — | — | — | — | | |

[a]N = number of tests.

What is claimed is:

1. A method of administering a therapeutic dose of an opioid to the systemic circulation of a mammal which comprises topically administering to the mammal an opioid-containing pharmaceutical composition, wherein the composition consists essentially of a therapeutically effective amount of an opioid or a pharmaceutically acceptable salt thereof; an effective penetration enhancing amount of at least one of a saturated fatty acid of 8–15 carbon atoms or of an unsaturated fatty acid of 8–18 carbon atoms; and propylene glycol as a suitable pharmaceutical carrier.

2. A method according to claim 1 wherein the opioid is a natural or synthetic opioid analgesic such as morphine, oxymorphone, fentanyl, meperidine, propoxyphene, or oxycodone; a natural or synthetic narcotic antagonist such as nalmefene, naloxone, or naltrexone; a natural or synthetic mixed opioid agonist/antagonist such as nalbuphine, butorphanol, buprenorphine or pentazocine; or a pharmaceutically acceptable salt thereof.

3. A method according to claim 2 wherein the saturated fatty acid has from 10 to 15 carbon atoms and the unsaturated fatty acid has 10 to 15 carbon atoms.

4. A method according to claim 3 wherein the fatty acid has 14 carbon atoms.

5. A method according to claim 4 wherein the fatty acid is myristic acid.

6. A method according to claim 5 wherein the vehicle is propylene glycol.

7. A method according to claim 3 wherein the composition is in lotion or cream form.

8. A method according to claim 7 wherein the composition comprises 1 to 15% opioid, 30 to 80% vehicle, and 1 to 45% fatty acid.

9. A method according to claim 7 wherein the composition comprises 5 to 15% opioid, 30 to 80% propylene glycol, 2 to 25% fatty acid.

10. A method according to claim 8 wherein the composition further comprises water as an emulsifying agent to provide a composition in emulsion form.

11. A method according to claim 10 wherein the composition contains from about 30 to 50% water.

12. A method according to claim 8 wherein the composition further comprises a polymeric substance to provide a composition in gel form, said polymeric substance selected from ethylcellulose, hydroxypropylcellulose or a mixture thereof.

13. A method according to claim 12 wherein the composition contains from about 20 to 30% polymeric substance.

14. A pharmaceutical composition effective in producing transdermal delivery of a therapeutically effective amount of an opioid to the systemic circulation of a mammal, the composition consisting essentially of a therapeutically effective amount of an opioid or a pharmaceutically acceptable salt thereof; an effective penetration enhancing amount of at least one of a saturated fatty acid of 8–15 carbon atoms or of an unsaturated fatty acid of 8–18 carbon atoms; and propylene glycol as a suitable pharmaceutical carrier.

15. A composition according to claim 14 wherein the opioid is a natural or synthetic opioid analgesic such as morphine, oxymorphone, fentanyl, meperidine, propoxyphene, or oxycodone; a natural or synthetic narcotic antagonist such as nalmefene, naloxone, or naltrexone; a natural or synthetic mixed opioid agonist/antagonist such as nalbuphine, butorphanol, buprenorphine or pentazocine; or a pharmaceutically acceptable salt thereof.

16. A composition according to claim 15 wherein the saturated fatty acid has from 10 to 15 carbon atoms and the unsaturated fatty acid has 10 to 15 carbon atoms.

17. A composition according to claim 16 wherein the fatty acid has 14 carbon atoms.

18. A composition according to claim 11 wherein the fatty acid is myristic acid.

19. A composition according to claim 10 wherein the vehicle is propylene glycol.

20. A composition according to claim 16 wherein the composition is in lotion or cream form.

21. A composition according to claim 11 which comprises 1 to 15% opioid, 30 to 80% vehicle, and 1 to 45% fatty acid, and the balance being an excipient.

22. A composition according to claim 21 which comprises 5 to 15% opioid, 30 to 80% propylene glycol, 2 to 25% fatty acid, and the balance being an excipient.

23. A composition according to claim 21 which further comprises water and an emulsifying agent to provide a composition in emulsion form.

24. A composition according to claim 23 which contains from about 30 to 50% water.

25. A composition according to claim 21 which further comprises a polymeric substance to provide a composition in gel form, said polymeric substance selected from ethylcellulose, hydroxypropylcellulose or a mixture thereof.

26. A composition according to claim 25 which contains from about 20 to 30% polymeric substance.

27. The composition of claim 22 which comprises about 10% oxymorphone, about 10% myristic acid, about 55% propylene glycol, and about 25% of ethylcellulose, hydroxypropylcellulose, or a combination of both.

* * * * *